United States Patent
Heindl et al.

(10) Patent No.: US 7,695,980 B2
(45) Date of Patent: Apr. 13, 2010

(54) CHEMILUMINESCENT COMPOUNDS AND THEIR USE

(75) Inventors: Dieter Heindl, Paehl (DE); Rupert Herrmann, Weilheim (DE); Wolfgang Jenni, Munich (DE); Heribert Maerz, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 907 days.

(21) Appl. No.: 11/339,454

(22) Filed: Jan. 25, 2006

(65) Prior Publication Data
US 2006/0199833 A1 Sep. 7, 2006

Related U.S. Application Data

(63) Continuation of application No. PCT/EP2004/008413, filed on Jul. 28, 2004.

(30) Foreign Application Priority Data
Jul. 30, 2003 (EP) .................. 03016621

(51) Int. Cl.
| | |
|---|---|
| G01N 33/533 | (2006.01) |
| C07K 1/13 | (2006.01) |
| C07D 333/50 | (2006.01) |
| C07D 307/92 | (2006.01) |

(52) U.S. Cl. .................. 436/546; 436/56; 436/128; 436/129; 436/800; 436/544; 530/402; 530/406; 549/43; 549/458

(58) Field of Classification Search .................. 436/544, 436/546, 56; 530/402, 403; 549/43, 429, 549/432, 458
See application file for complete search history.

(56) References Cited

U.S. PATENT DOCUMENTS

| 5,326,876 A | 7/1994 | Kawata |
| 5,589,328 A | 12/1996 | Mahant |
| 5,669,819 A | 9/1997 | Mattingly et al. |
| 5,681,958 A | 10/1997 | Bierer |
| 5,723,295 A * | 3/1998 | Akhavan-Tafti et al. ........ 435/6 |

FOREIGN PATENT DOCUMENTS

| DE | 3645292 C2 | 2/1988 |
| EP | 0617288 B1 | 5/2002 |
| WO | WO 95/19976 | 7/1995 |
| WO | WO 98/56756 | 12/1998 |

OTHER PUBLICATIONS

Chovin, P. et al., "Research on colored lactones. Structure of Pechmann dyes, of isoindigo and of naphthyrones," Bulletin de la Societe Chimique de France 12 (1945) 105-111.

(Continued)

Primary Examiner—Shafiqul Haq
(74) Attorney, Agent, or Firm—Marilyn Amick; Roche Diagnostics Operations, Inc.

(57) ABSTRACT

The present invention relates to novel chemiluminescent compounds, to a method for synthesizing these compounds, to derivatives and conjugates comprising these compounds, to the use of these compounds or conjugates thereof in chemiluminescence based assays, especially in immunoassays.

14 Claims, 5 Drawing Sheets

OTHER PUBLICATIONS

Naturforsch, z., "Pyrroloquinolines, Part III [1] Synthesis of 1H-Pyrrolo (2,3-b) quinolines," 35b, 746-748 (1980).

Treibs, W. et al., "Pseudoaramatics from 2-indanonene,IV," Liebigs Ann. Chem, Bd. 642 (1961) 97-99.

Adamczyk, M. et al., "Modulation of the Chemiluminescent Signal from N10-(3Sulfopropyl)-N-Sulfonylacridinium-9-carboxamides," Tetrahedron 55 (1999) 10899-10914.

Adamczyk, M. et al., "Neopentyl 3-Triflyloxypropanesulfonate. A Reactive Sulfopropylation Reagent for the Preparation of Chemiluminescent Labels," J. Org. Chem. 1998, 63, 5636-5639.

Aslam, M. et al., Bioconjugation (1998) 216-363, London.

Bierer, D. et al., "Antihyperglycemic Activities of Cryptolepine Analogues: An Ethnobotanical Lead Structure Isolated from Cryptolepis sanguinolenta," J. Med. Chem. 1998, 41, 2754-2764.

Degutis, Y. et al., "Alkylation of Quindoline and Quindoline-11-Carboxylic Acid," Chemistry of Heterocyclic Compounds 10 (1986)1114-1117.

Dodeigne, C. et al., "Chemiluminescence as diagnostic tool. A review.," Talanta 51 (2000) 415-439.

Flanagan, J. et al., "Functionalized Tricarbocyanine Dyes as Near-Infrared Fluorescent Probes for Biomolecules," Bioconjugate Chem. 1997, 8, 751-756.

Holt. S. et al., "Carbazoles, Carbolines, and Related Compounds. Part II. Quinindoline Derivatives," Journal of Chemical Society (1948) 922-924.

Kessler, C., "Non-radioactive labeling and detection of biomolecules," Springer Verlag, Berlin Heidelberg (1992).

Lakshiminarayana, P. et al., "Synthesis of 4-Carboxy-2, 3-Dihydrofuro (2,6-b) Quinoline," Tetrahedron Letters No. 57, pp. 4947-4948, 1970.

Lisowski, V. et al., "Efficient Synthesis of Novel 3-(Het)arylanthranilic Acids via a Suzuki Cross-Coupling Reaction of 7*Iodoisatin with (Het)arylboronic Acids in Water," J. Org. Chem. 2000, 65, 4193-4194.

Los, M. et al., "Heterocyclic Analogues of Azulene," Journal of the Chemical Society (1959) 1680-1685.

March, J. Advance Org. Chem. $4^{th}$ edition (1992) 539-542.

Mayer, A. et al., "Luminescent Labels-More than Just an Alternative to Radioscopes?" Angewandte Chem. Intern. Ed. Engl. 33(1994) 1044-1072.

McCapra, F. et al., "Luminescent Labels for Immunoassay-From Concept to Practice," Journal of Bioluminescence and Chemiluminescence, vol. 4, 51-58 (1989).

Mohan, P.S. et al., "Pyrroloquinolines: Part V—A Convenient synthesis of 1 H-pyrrolo[2,3-b] quinolines," Indiana Journal of Chemistry, vol. 28B, Marcy 1989, pp. 270-271.

Piggott, M. et al., "The Synthesis of Ventilone A," Aust. J. Chemc. 2000, 53, 749-754.

Rajamanickam, P. et al., "A Convenient Synthesis of Benzo [c] [2,6] naphthyridines," Synthesis 5 (1985) 541-543.

Shanmugam, P. et al., "Thienoquinolines, II A New and Convenent Synthesis of Thieno (2,3-b) quinoline," Z. Naturforsch. B. Chem. Sciences 31 (1976) 1297-1298.

Shanmugam, P. et al., "A New Synthesis of Furo(2,3-b) quinoline," Z. Naturforsch B. Chem. Sciences 27 (1972) 474-476.

Soundararajan, S. et al., "Boronic Acids for Affinity Chromatography: Spectral Methods for Determinations of Ionization and Diol-Binding Constants," Analytical Biochemistry178, 125-134 (1989).

Tijssen, "Practice and Theory of Enzyme Immunoassays," (1990) Amsterdam, Elsevier.

Waldrop, A. et al., "Chemiluminescent determination of hydrogen peroxide with 9-acridinecarbonylimidazole and use in measurement of glucose oxidase and alkaline phosphotase activity," Luminescence 2000; 15:169-182.

Sheibley, F. et al., "3,5-Dichloraniline in Sandmeyer's Isatin Synthesis. 4,6-Dichloranthranilic Acid," J. Org. Chem. 21(1956) 171-173.

* cited by examiner

CHEMILUMINESCENT COMPOUNDS AND THEIR USE

RELATED APPLICATIONS

This application is a continuation of PCT/EP2004/008413 filed Jul. 28, 2004 which claims priority to European application EP 03016621.9 filed Jul. 30, 2003.

FIELD OF THE INVENTION

The present invention relates to novel chemiluminescent compounds of general Formula I:

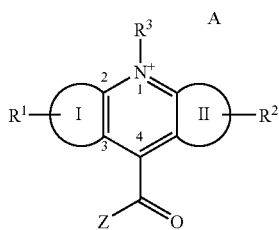

wherein:
the fused rings I or II represent an aromatic five ring heterocycle or an aryl ring, respectively, with the proviso that at least one of I or II is an aromatic five ring heterocycle,
$R^1$ and $R^2$ independently represent hydrogen, R, halogen, —$NR_2$, —OR, —OH, —$S(O)_2OH$, —CN, —SCN, —SSR, —SR, —C(O)R, —C(O)H, —C(O)OR, —C(O)OH, —NHC(O)R, —C(O)NHR, —$C(O)NH_2$, —$S(O)_2NHR$ or —$S(O)_2NH_2$;
and R represents alkyl, alkenyl, alkynyl or aralkyl, wherein said alkyl, alkenyl or alkynyl can contain up to 20 heteroatoms,
$R^3$ represents alkyl, alkenyl, alkynyl or aralkyl, wherein said alkyl, alkenyl or alkynyl can contain up to 20 heteroatoms, and may also contain a coupling moiety,
Z represents a leaving group, and
A, if required, represents a counter-ion to balance a net charge of the compound.

The invention also relates to a method for synthesizing the compounds of Formula I, to derivatives and conjugates comprising these compounds, to the use of these compounds or conjugates thereof in chemiluminescence based assays, especially in immunoassays.

BACKGROUND OF THE INVENTION

The specific detection and quantification of biological molecules has been accomplished with excellent sensitivity for example by the use of radio-labeled reporter molecules. The first radio immunoassays developed in the end of the 1950's have matured into the most important tools of in vitro diagnostics, especially in medicine, using a broad variety of different detection or reporter systems. Well-known examples of reporter molecules are enzymes, labeled latex beads, fluorescent dyes and especially chemiluminescent dyes.

Reviews describing the theory and practice of specific binding assays are available. The skilled artisan will find all necessary technical details for performing specific binding assays in textbooks like Tijssen, "Practice and theory of enzyme immunoassays" (1990) Amsterdam, Elsevier and various editions of Colowick, S. P., and Caplan, N. O., Methods in Enzymology (1980-1986), Academic Press, dealing with immunological detection methods, especially volumes 70, 73, 74, 84, 92 and 121.

Paralleled by the development of light measuring techniques and the commercial availability of highly sensitive apparatuses, luminophores have in many applications replaced isotopic labels. Some of the new luminescent labels facilitate analyte detection at extremely low levels of sensitivity. Therefore such labels also commercially are very interesting.

Luminescent labels may be subdivided into the group of fluorescent labels and the group of luminescent labels. Whereas fluorescent labels require irradiation of a sample with excitation light in order to detect and measure the fluorescent label present, the luminescent systems, e.g., chemiluminescent systems do not require an extra source of light.

A widely used class of chemiluminescent labels are the acridinium compounds. Their mechanism of chemiluminescence has been extensively studied and is nicely summarized in a review article published by Mayer, A., and Neuenhofer, S., Angewandte Chem. Intern. Ed. Engl. 33 (1994) 1044-1072, Weinheim, VCH Verlagsgesellschaft mbH, as well as in a review article by Dodeigne, C., et al., Talanta (2000) 415-438.

Several mechanisms leading to emission of light according to the chemiluminescence principles have been proposed. Short-lived intermediates are considered part of the processes leading to decarboxylation and emission of light. The processes postulated for acridinium ester labels, resulting in emission of light or in the unwanted side reaction (dark reaction) leading to hydrolysis of the ester, are schematically shown in FIG. 1.

According to the proposed mechanism the carbonyl group (which has been part of the amide or ester bond) by attack of $H_2O_2$ becomes part of a dioxetanone moiety. Spontaneous decomposition of the dioxetanone moiety is accompanied by light emission and yields a heterocyclic ketone and $CO_2$ in case of a carbonyl group, or in more general chemical terms a heterocumulene in case functional equivalents of the carbonyl group had been present.

It is instantly evident from FIG. 1, that the light reaction (LR) and the dark processes (DP) both are dependent on the properties of the leaving group Z.

An essential feature of the acridinium esters used in diagnostic applications is that the ester function has been substituted to carry a suitable leaving group Z. Suitable leaving groups are designed to match as good as possible two essential requirements: stability and high quantum yield.

On the one hand the leaving group of an acridinium esters must be as active as possible, i.e., leaving quite readily under measurement conditions, to allow for a sensitive detection and high quantum yield. This high activity on the other hand, however, goes to the expense of instability towards hydrolysis. Such instabilities are even more critical if such chemiluminescent labels are used for conjugation to biomolecules. The goal to achieve a high chemiluminescence yield and in addition a high stability of the labeled reagent equals to a fine balance act always ending in a compromise between light yield and stability.

To at least partially reduce the problems encountered, new and different leaving groups have been designed and proposed.

EP 617 288 gives examples of appropriate leaving groups. Most popular are N-sulfonamides, e.g., described in U.S. Pat. No. 5,669,819, thioesters as described in DE 3 645 292, hydroxamic acid esters described in WO 98/56765, imidazolides as described by Waldrop III, A. A., et al., Luminescence 15 (2000) 169-182, and pyridinium amides (WO 95/19976).

Besides the acridinium labels, other well known chemiluminescence based systems make use of labels comprising amongst others the following categories, the combination of luciferins with corresponding luciferases, cyclic arylhydrazides, acridinium derivatives, stable dioxetanes, and oxalic acid derivatives.

However, overall only a rather limited number of chemiluminescent basic compounds is known and even less have proven useful for routine diagnostic applications.

SUMMARY OF THE INVENTION

It was the task of the present invention to find and identify a novel class of compounds appropriate for chemiluminescence assays which compounds provide for a stable chemiluminescent dye or label on the one hand and for sensitive detection or high quantum yield on the other hand. Such compounds additionally should be suitable for labeling of, or conjugation to a biomolecule, e.g., a specific binding partner. I.e., it should be possible to introduce a coupling group without impairing the chemiluminescence properties of such compounds and/or the compound itself should not interfere with the biomolecule.

It has been found that the compounds of Formula I are chemiluminescent. Since the compounds according to the present invention encompass both storage stability, as well as sensitive detection in chemiluminescent procedures they are also used to label biomolecules and the resulting conjugates with great advantage can be applied in appropriate specific binding assays for detection of an analyte in a sample.

DETAILED DESCRIPTION OF THE INVENTION

Figure 1:
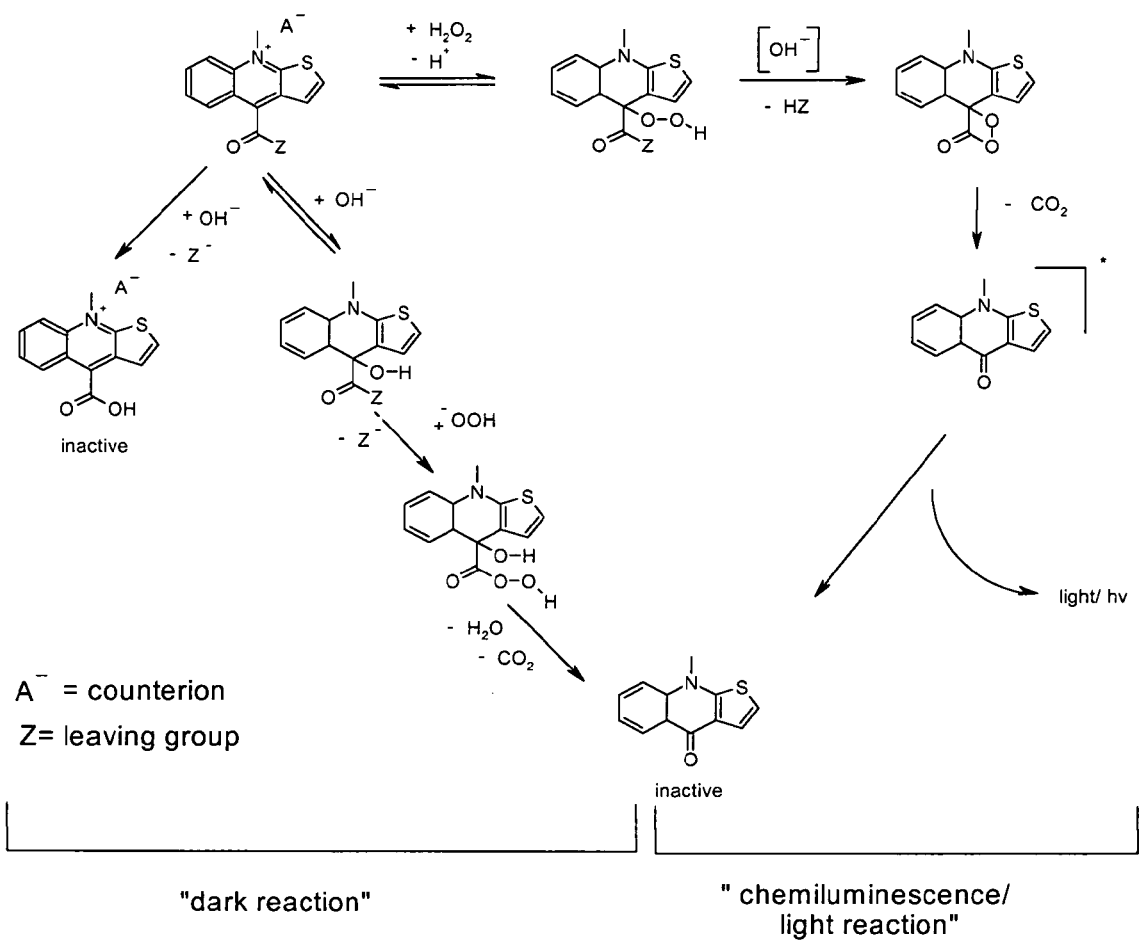
FIG. 1 Acridinium labels
Shown are postulated reaction mechanisms leading to chemiluminescence or non-luminescent decay. Both possible pathways are depicted. The light creating reaction, or light reaction (=LR) leads to chemiluminescence, whereas the dark reaction pathway, or dark process (DP) leads to direct hydrolysis not accompanied by light emission.

In a first embodiment the present invention relates to a compound of Formula I:

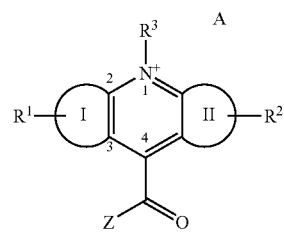

wherein:
the fused rings I or II represent an aromatic five ring heterocycle or an aryl ring, respectively, with the proviso that at least one of I or II is an aromatic five ring heterocycle,
$R^1$ and $R^2$ independently represent hydrogen, R, halogen, $-NR_2$, $-OR$, $-OH$, $-S(O)_2OH$, $-CN$, $-SCN$, $-SSR$, $-SR$, $-C(O)R$, $-C(O)H$, $-C(O)OR$, $-C(O)OH$, $-NHC(O)R$, $-C(O)NHR$, $-C(O)NH_2$, $-S(O)_2NHR$ or $-S(O)_2NH_2$;
and R represents alkyl, alkenyl, alkynyl or aralkyl, wherein said alkyl, alkenyl or alkynyl can contain up to 20 heteroatoms,
$R^3$ represents alkyl, alkenyl, alkynyl or aralkyl, wherein said alkyl, alkenyl or alkynyl can contain up to 20 heteroatoms, and may also contain a coupling moiety,
Z represents a leaving group, and
A, if required, represents a counter-ion to balance a net charge of the compound.

$R^1$ and $R^2$ represent preferably hydrogen fluorine, chlorine, $-OH$, $-C(O)CH_3$, $-S(O)_2OH$, $-S(O)_2NH_2$ or $-S(O)_2NHR$, wherein R is defined as above. Preferably said substituents are fluorine, chlorine, $-OH$, $-C(O)CH_3$, $-S(O)_2OH$ or $-S(O)_2NH_2$, especially fluorine, chlorine, $-OH$ or $-C(O)CH_3$.

The group $R^3$ preferably is selected from alkyl, sulfoalkyl or alkylamidoalkyl.

The group $R^3$ is further on preferably selected from alkyl or sulfoalkyl.

More preferred $R^3$ is selected from methyl, ethyl, sulfopropyl and sulfobutyl.

Optionally $R^3$ also comprises a coupling moiety capable of attaching the compound to a protein, a nucleic acid or a specific binding material. Preferably said coupling moiety is selected from the group consisting of N-succinimidyl-oxycarbonyl, maleinimido, 4,6-dichloro-[1,3,5]triazin-2-amino-, N-benzotriazolyl-oxycarbonyl, N-phtalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, $-C(O)Cl$, $-C(O)Br$, $-C(O)I$, $-SO_2Cl$, $-SO_2Br$, $-SO_2I$, $-NH_2$, $-N_3$, $-N=C=O$, $-N=C=S$, $-N_2^+$, $-Cl$, $-Br$ or $-I$.

Further preferred the coupling moiety is selected from the group consisting of N-succinimidyl-oxycarbonyl, N-benzotriazolyl-oxycarbonyl, maleinimido, N-phtalimidyl-oxycarbonyl, aryloxycarbonyl as e.g. p-nitrophenyl-oxycarbonyl or pentafluorophenyl-oxycarbonyl, imidate, p-aminobenzoyl, $-C(O)Cl$, $-C(O)Br$, $-SO_2Cl$, $-NH_2$, $-N_3$. More preferred the coupling moiety is a N-succinimidyl-oxycarbonyl group or $-SO_2Cl$. Especially preferred the coupling moiety is a N-succinimidyl-oxycarbonyl.

The net charge of a compound according to Formula I obviously will depend on the sum of all charges present. In case the residues $R^1$ to $R^3$ do not contribute to the net charge of the compound of Formula I, it will comprise a single positive net charge due to its oxidized nitrogen. The counter-ion A required will then comprise a single negative charge (=A⁻). The counter-ion A⁻ preferably represents halide, $CH_3SO_4^-$, $CF_3SO_3^-$, $FSO_3^-$, $C_4F_9SO_3^-$, or $CH_3C_6H_4SO_3^-$.

In case the residues $R^1$ to $R^3$ do contribute to the net charge of the compound of Formula I and A represents an cation, it is preferably selected from the group consisting of $K^+$, $Na^+$, tetraalkylammonium.

The term "aromatic five ring heterocycle" as used herein means an aromatic five ring system, which contains up to three, preferably one or two, more preferred only one, heteroatom(s) selected independently from N, O or S and the remaining ring atoms being carbon atoms. Examples of such aromatic five ring heterocycle include pyrrole, thiophene, furan, thiazole, oxazole, imidazole; pyrazole and triazole, preferably pyrrole, thiophene and furan and especially preferred thiophene and furan.

Optionally such aromatic five ring heterocycle can further be fused with a benzene ring. Examples of such (benzene-fused) aromatic five ring heterocycle are indole, benzothiophene, benzofuran. The substituents $R^1$ or $R^2$ in such (benzene-fused) aromatic five ring heterocycle are located at the benzene part.

In a preferred embodiment of the invention the aromatic five ring heterocycle is not fused with a benzene ring.

In another preferred embodiment of the invention the aromatic five ring heterocycle is fused with a benzene ring.

The term "aryl" as used herein means a monocyclic or a condensed polycyclic aromatic hydrocarbon group, preferably exemplified by C6-10 aryl groups such as phenyl or naphthyl. Preferably aryl is phenyl.

The compound according to Formula I may contain one or two aromatic five-ring heterocycles as defined above. In case two aromatic five ring heterocycles are present, ring I and ring II may be the same or different. Preferably ring I and ring II are identical and represent a mirror image with respect to the central axis (atoms 1 and 4) of Formula I.

In another preferred embodiment of the invention only one of the rings I or II represents an aromatic five ring heterocycle as defined above while the other represents aryl as defined above.

As the skilled artisan will appreciate, any of the aromatic rings I or II of Formula I may comprise one or more of the substitutions $R^1$ and $R^2$, as defined above. Up to four such substituents, preferably up o two such substituents, may be present at an aryl ring or benzene-fused aromatic five ring heterocycle, if present, and up to two substituents, preferably one substituent, may be present per aromatic five ring heterocycle. Preferably, only one of $R^1$ or $R^2$ as defined above is present.

The leaving group Z is selected from —O—V, —S—V, —N(V)—SO₂—V', —O—N(V)—SO₂—V', —S—N(V)—V', —O—N(V)—C(O)—V', —O—N=C(V)—V' or —O—N=C(V)—Cl, wherein:
V or V' independently represent alkyl, which is optionally substituted 1 or 2 times by —S(O)₂OH or 1 to 5 times by fluorine or chlorine, preferably fluorine; and/or V or V' independently represent an aryl moiety corresponding to the following formula:

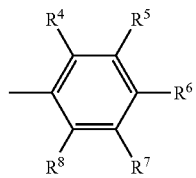

wherein $R^4$ and $R^8$ independently represent hydrogen, halogen, alkyl, alkenyl, alkynyl, alkoxy, alkylsulfanyl or alkylamido, $R^5$ and $R^7$ are as defined as $R^1$ and $R^2$, $R^6$ represents —$R^9$—$R^{10}$, wherein $R^9$ if present, represents alkyl, alkenyl, alkynyl or alkylamido wherein said alkyl, alkenyl or alkynyl can contain up to 20 heteroatoms, or $R^9$ if present, represents an electron-withdrawing group, and $R^{10}$, if present, represents a coupling moiety which is defined as above the coupling moiety optionally comprised in $R^3$. As the skilled artisan will appreciate, such a coupling moiety is present only once in either $R^3$ or $R^6$.

$R^5$ and $R^6$, and $R^7$ and $R^6$ are interchangeable.

The electron-withdrawing group present in $R^9$ preferably is selected from —NO₂, —CN, —Cl or —N⁺(CH₃)₃, alkylcarbonyl or alkoxycarbonyl, wherein the alkyl or the alkoxy part is optionally substituted once by aryl.

Preferably Z represents —O—V, —S—V or —NV—SO₂—V' and especially preferred Z represents —O—V or —NV—SO₂—V'.

The pKa-value of the leaving group Z is among other aspects essential for the chemiluminescence quantum yield on the one hand and for the stability against hydrolysis on the other hand (McCapra, F., et al., J. Biolumin. Chemilumin. 4 (1989) 51-58; Adamczyk, M., et al., Tetrahedron 55 (1999) 10899-10914). To meet these requirements, the pKa-value of the leaving group Z is preferably between 5.0 and 12.5. The corresponding pKa-value can be determined by the method of Soundararajan, S., et al., Analytical Biochemistry 178 (1989) 125-134. More preferred the leaving group Z has a pKa-value between 6.0 and 12.0.

The term "wherein said alkyl, alkenyl or alkynyl can contain up to 20 heteroatoms" refers to the corresponding foresaid alkyl, alkenyl or alkynyl groups. It means that said alkyl, alkenyl or alkynyl groups are optionally interrupted one to five times by —O—, —N(CH₃)—, —S—, —S(O)₂—, —S(O)₂O—, —OS(O)₂—, —S(O)₂NH—, —NHS(O)₂—, —C(O)—, —OC(O), —C(O)O—, —NHC(O)— or —C(O)NH—, and said alkyl, alkenyl or alkynyl groups are optionally substituted one to five times with —S(O)₂OH, —OH, —C(O)OH, fluorine or chlorine such that not more than 20 heteroatoms, preferably not more than 15 heteroatoms, also preferably not more than 10 heteroatoms, are comprised in said alkyl, alkenyl or alkynyl groups. Preferably said alkyl, alkenyl or alkynyl groups are optionally interrupted by —O—, —NHC(O)— or —C(O)NH—, and said aliphatic hydrocarbon groups are optionally substituted by —S(O)₂OH, —OH, —C(O)OH.

The term "alkyl" denotes a straight-chain or branched saturated hydrocarbon group having 1 to 20, preferably 1 to 10, more preferred 1 to 5 carbon atoms. Examples of the "alkyl groups" include C1-20 alkyl groups, more preferred C1-10 alkyl groups such as methyl, ethyl, propyl, isopropyl, butyl, isobutyl, sec.-butyl, tert.-butyl, pentyl, isopentyl, neopentyl, tert.-pentyl, hexyl, isohexyl, heptyl, octyl, nonyl, decyl, 1,1-dimethylbutyl, 2,2-dimethylbutyl, 3,3-dimethylbutyl and 2-ethylbutyl.

The term "alkenyl" denotes an unsaturated straight-chain or branched aliphatic hydrocarbon group containing one double bond and having 2 to 20, preferably 2 to 10, more preferred 1 to 5 carbon atoms. Examples of the "alkenyl group" include C2-20 alkenyl groups, more preferred C2-10 alkenyl groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" denotes an unsaturated straight-chain or branched aliphatic hydrocarbon group containing one triple bond and having 2 to 20, preferably 2 to 10, more preferred 1 to 5 carbon atoms. Examples of the "alkynyl group" include C2-20 alkynyl groups, more preferred C2-10 alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "alkoxy" as used herein means an alkyl group as defined above, which is attached via an oxygen-atom.

The term "alkylsulfanyl" as used herein means an alkyl group as defined above, which is attached via an sulfur-atom.

The term "alkylamido" as used herein means an alkyl group as defined above, which is attached via —C(O)NH— or —NHC(O)—.

The term "sulfoalkyl" as used herein means an alkyl group as defined above, which is substituted by —SO$_3$H.

The term "alkylamidoalkyl" means an alkyl group as defined above, which is interrupted once by —C(O)NH— or —NHC(O)—

The term "alkylcarbonyl-oxycarbonyl" means an alkyl group as defined above, which is attached via —C(O)OC(O)— and which is optionally substituted one or several times by —NO$_2$, halogen or —N$^+$(CH$_3$)$_3$.

The term "alkoxycarbonyl" means an alkyl group as defined above, which is attached via —OC(O)— and which is optionally substituted one or several times by —NO$_2$, halogen or —N$^+$(CH$_3$)$_3$.

The term "aralkyl" as used herein denotes an aryl group as defined above attached to a straight chain or branched alkylene group having 1 to 15, preferably 1 to 10, more preferred 1 to 5 carbon atoms,. Example of such groups are benzyl, 1-phenethyl, 2-phenethyl as well as phenpropyl and phenbutyl together with their isomers.

The term "arylcarbonyl-oxycarbonyl" means an aryl group as defined above, which is attached via —C(O)OC(O)— and which is optionally substituted one or several times by —NO$_2$, —CN, halogen, —C(O)CH$_3$ or —N$^+$(CH$_3$)$_3$.

The term "aryloxycarbonyl" means an aryl group as defined above, which is attached via —OC(O)— and which is optionally substituted one or several times by —NO$_2$, —CN, halogen, —C(O)CH$_3$ or —N$^+$(CH$_3$)$_3$.

The term "halogen" means fluorine, chlorine, bromine and iodine, especially fluorine and chlorine.

The term "imidate" means an alkyl group or an aryl group as defined above, which is attached via —OC(=NH)—.

The compounds of the general Formula I may be prepared by any process known to be applicable for the preparation of chemically-related compounds by the one skilled in the art. Such processes, when used to prepare the compounds of Formula I are illustrated by the following representative examples of scheme 1 in which, unless otherwise stated, R$^1$, R$^2$, R$^3$, Z and A have the significance given herein before. Ring I is an aryl ring or an aromatic five ring heterocycle while ring II is an aromatic five ring heterocycle.

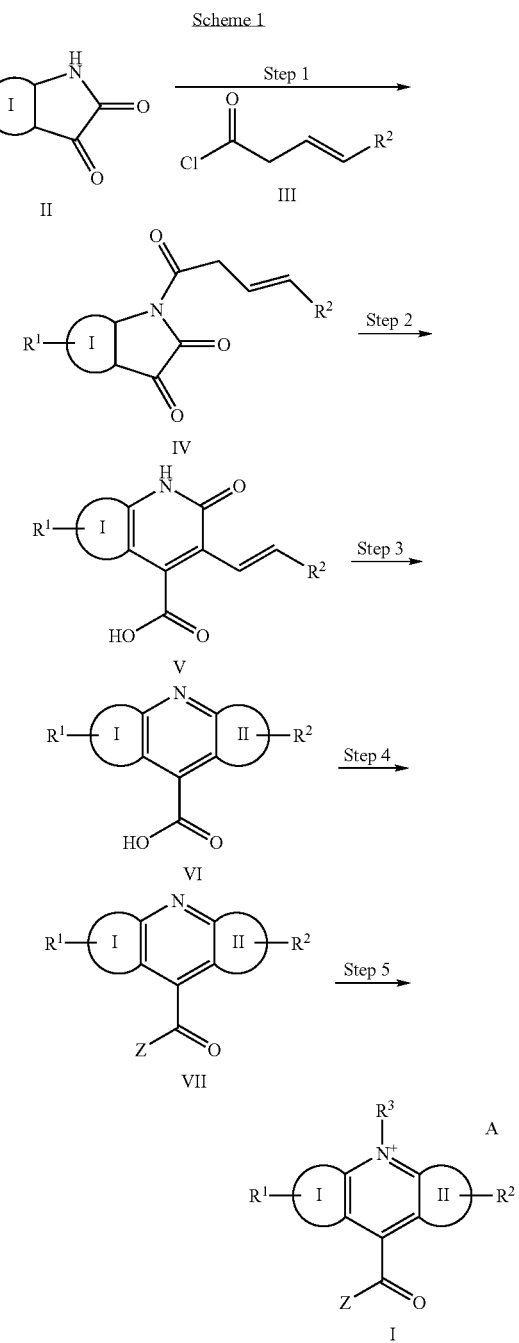

A preferred method for the synthesis of the compounds of Formula I starts from the corresponding pyrroledione derivatives of Formula II.

The necessary starting compounds of Formula II are either commercially available or may be obtained by standard procedures of organic chemistry, e.g. by reaction of a corresponding aromatic amine (arylamines or heteroarylamines) with oxalylchloride. The reaction starts with an N-acylation, followed by an intramolecular acylation which can be catalyzed by Lewis acids. (e.g. Piggott, M. J. and Wege, D., Australian Journal of Chemistry 53 (2000) 749-754; March, J., Advanced Organic Chemistry 4th ed. (1992) 539-542) More often the corresponding aromatic amines (arylamines or heteroarylamines) are reacted with chloral hydrate (2,2,2-trichlor-1,1-ethanediol) and hydroxylamine (hydrochloride) (via the hydroxyiminoacetamides) in a cyclization reaction to the compounds of Formula II (e.g. Sheibley, F. E. and McNulty, J. S., J. Org. Chem. 21 (1956) 171-173; Lisowski, V, et al., J. Org. Chem. 65 (2000) 4193-4194).

In Step 1 the pyrroledione derivatives of Formula II are acylated by the optionally substituted vinyl acetyl chlorides of Formula III to yield the compounds of Formula IV (Lakshminarayana, P., et al., Tetrahedron Lett. 11 (1970) 4947-4948; Rajamanickam, P. and Shanmugam, P., Synthesis 5 (1985) 541-543). Alternatively other activated vinyl acetyl derivatives can be used.

Step 2: The acylated compounds of Formula IV are converted (often directly without isolation) in a Pfitzinger rearrangement using sodium or potassium hydroxide at temperatures around 100° C. to the corresponding carboxylic acids of Formula V.

Step 3: Depending on the nature ring II (which is an aromatic five ring heterocycle) different reaction sequences are performed to obtain the cyclized compounds of Formula VI. For this purpose the carboxylic acid moiety of Formula V is usually protected (e.g. as methyl ester with diazomethane (Shanmugam, P., et al., Z. Naturforsch. B: Chem. Sciences 31 (1976) 1297-1298) and the protecting group is cleaved in the last reaction step of the sequence (e.g. by saponification of the esters) to yield the free carboxylic acids of Formula VI.

If the aromatic five ring heterocycle II is furan (e.g. Shanmugam, P. and Lakshminarayana, P., Z. Naturforsch. B: Chem. Sciences 27 (1972) 474-476) the acid protected derivatives of Formula V are cyclized with bromine in the presence of a non-nucleophilic base (e.g. triethylamine, diisopropylethylamine and the like) under heating. Thus the acid protected furan derivatives of Formula VI are obtained which are then deprotected to the free acids of Formula VI.

If the aromatic five ring heterocycle II is thiophene (e.g. Shanmugam, P., et al., Z. Naturforsch. B: Chem. Sciences 31 (1976) 1297-1298) the acid protected derivatives of Formula V are converted first into their chlorinated species by treatment with phosphoryl chloride (or other chlorinating agents like phosphorus pentachloride). Thus the oxo-substituent on the central ring is substituted by chlorine (analogously to the imino chloride formation from amides). Next steps are the addition of bromine and the subsequent treatment of the resulting dibromo derivative with thiourea under heating which yields the acid protected thiophene derivatives of Formula VI. Deprotection then affords the free acids of Formula VI.

If the aromatic five ring heterocycle II is pyrrol (e.g. Mohan, P.S., et al., Z. Naturforsch. B: Chem. Sciences 35 (1980) 746-748; Ramasamy, K. and Shanmugam, P., Indian J. Chem. 28B (1989) 270-271) the acid protected derivatives of Formula V are also (see furans above) converted first into their chlorinated species by treatment with phosphoryl chloride (or other chlorinating agents like phosphorus pentachloride). Then two alternative routes can be performed: One is the bromination, the subsequent reaction with p-amino benzene sulfonamide under heating (fusion at ~170° C.) and the treatment with potassium (or sodium) hydroxide and afterwards a non-nucleophilic base (e.g. triethylamine, diisopropylethylamine and the like) which affords the free acids of Formula VI (if the protecting group is a methyl ester or the like) or the acid protected pyrrol derivatives of Formula VI. If necessary, deprotection affords the free acids of Formula VI.

Alternatively the chlorinated species is cyclized in a nucleophilic reaction with ammonia or aliphatic amines to a dihydropyrrol derivative, which is dehydrogenated (e.g. with 2,3-dichloro-5,6-dicyano-p-benzoquinone (DDQ)) to the acid protected pyrrol derivatives of Formula VI. Deprotection affords the free acids of Formula VI.

Another possibility to obtain the acids of Formula VI is the oxidation of the corresponding methyl derivatives, which is either carried out either in one (e.g. with potassium permanganate, chromic acid and the like) or two steps (first: $SeO_2$, $CrO_2Cl_2$, $CrO_3/Ac_2O$, ceric ammonium nitrate and the like; second: silver (I) oxide, potassium permanganate, chromic acid, hydrogen peroxide)

In Step 4 of the reaction scheme 1 the leaving group Z is introduced. This reaction is normally carried out in a two step procedure.

In the first step, the carboxylic acid of the Formula VI becomes activated. This reaction is carried out in an inert solvent or diluent, for example, in dichloromethane, dioxane, tetrahydrofuran (THF) or N,N-dimethylformamide (DMF) in the presence of an activating agent. Suitable activating agents are, for example, oxalyl or thionyl chloride, isobutyl chloroformate, N-hydroxybenzotriazole, N,N'-carbonyldiimidazole, dicyclohexylcarbodiimide, N-(3-dimethylaminopropyl)-N'-ethylcarbodiimide (EDC), 2-morpholino-ethylisocyanide (MEI) and the like. Other activating agents can also be used and are well known to the skilled artist. The activated carboxylic acid derivative (e.g. the acid chloride) can be sometimes isolated as intermediate. Nevertheless the reaction is often carried out in a one-pot procedure without isolation of the activated carboxlic acid intermediate.

In the second step, the leaving group Z is introduced by adding Z (e.g. as a solution of its anion formed by reaction with a non-nucleophilic base like e.g. sodium hydride, triethylamine or diisopropylethylamine) to the activated carboxylic acid yielding the compounds of Formula VII. This reaction can be catalyzed sometimes by N,N-dimethylaminopyridine (DMAP) and the like. These methods are well known to those skilled in the art and depending of the nature of the leaving group Z different activation reactions may be suitable.

The leaving group Z might bear an suitable protecting group e.g. for an carboxylic acid moiety which can be comprised in Z. Such protecting groups can be e.g. t-butyl, t-butyl-dimethyl-silyl, benzyl, ethyl or other appropriate protecting groups known in the art. After the introduction of Z, such protecting groups can be cleaved to release e.g. a free carboxylic acid moiety. Such carboxylic acid moiety can then be converted into coupling moiety e.g. N-succinimidyl-oxycarbonyl by activating the carboxylic acid and reacting the activated acid intermediate with N-hydroxysuccinimide (HOSu). Also other coupling moieties can be introduced in such a carboxylic acid group. And furthermore other protected functional groups like acylated or silylated amino groups can be present in Z.

The cleavage of a protecting group in Z and/or the introduction of an optional coupling moiety in Z is either performed after Step 4 (Introduction of the leaving group Z). Or alternatively the cleavage of the protecting group in Z as well as the introduction of the optional coupling moiety in Z is carried out after Step 5 (N-alkylation).

Step 5 of the reaction sequence (scheme 1) is an N-alkylation of the nitrogen of the 1-position of compounds of Formula VII. For the N-alkylation different methods are known. Conventionally compounds of Formula VII are reacted with alkyl halides, especially alkyl iodides or bromides (e.g. MeI, EtI, EtBr and the like) or with trifluoromethyl-, methyl- or p-toluolene-sulfonates (e.g. MeOTf) to afford the corresponding compounds of Formula I. Alternatively tetralkyl boronium salts (e.g. $Me_4B^+BF_4^-$) can be used. The counterion A, which depends on the alkylating reagent used, can be exchanged by known methods so that for example the solubility of compounds of Formula I can be altered.

For the introduction of sulfoalkyl groups at the 1-position of compounds of Formula V, usually the corresponding sultone (cyclic alkylsulfonate) is used as alkylating agent (Flanagan, J. H., et al., Bioconjugate Chem. 8 (1997) 751-756; Adamczyk, M., et al., J. Org Chem. 63 (1998) 5636-5639). Lewis acids (e.g. $BF_3$-$Et_2O$) can higher the yields (U.S. Pat. No. 5,326,876). Alternatively the sulfopropylation can be preformed with the more reactive O-protected neopentyl 3-triflyloxypropanesulfonate (Adamczyk, M., et al., J. Org Chem. 63 (1998) 5636-5639), wherein the neopentyl protecting group is cleaved after alkylation to release the free sulfo group.

The intermediates of Formula VII are also subject of the present invention.

The compounds according to the present invention represent very attractive labels, e.g., for labeling of biomolecules. The methods used for coupling of labels to biomolecules have significantly matured during the past years and an excellent overview is given in Aslam, M., and Dent, A., Bioconjugation (1998) 216-363, London, and in the chapter "Macromolecule conjugation" in Tijssen, "Practice and theory of enzyme immunoassays" (1990), Elsevier, Amsterdam.

Appropriate coupling chemistries are known from the above cited literature (Aslam, supra). The chemical compound according to the present invention preferably is designed and synthesized to comprise a coupling group or coupling moiety which matches the coupling chemistry appropriate for the biomolecule under investigation.

In a preferred embodiment the chemical compound according to the present invention comprises only one coupling moiety within $R^3$ or $R^6$. Preferably the coupling moiety is part of $R^6$.

The coupling moiety is a reactive group or activated group which is used for chemically coupling of the compound to a biomolecule. As the skilled artisan will appreciate the coupling moiety is selected to match the chemical function on the biomolecule to which coupling shall be performed.

The chemiluminescent compounds of the present invention, depending on which coupling moiety is selected, can be reacted directly with the biomolecule either in an aqueous or an organic medium.

The chemiluminescent labels can be either directly attached to the biomolecule or connected to the biomolecule via a spacer to form a chemiluminescent conjugate comprising the biomolecule and a compound of the present invention. An example of preparing an Anti-TSH conjugate (i.e., a conjugate comprising an antibody to TSH and a compound according to Formula I) is provided in the examples section.

Amino groups of biomolecules (the terminal —$NH_2$ group or the $NH_2$ group of a lysine side chain, as well as ω-amino groups of diamino carboxylic acids) can be used for chemical coupling of a marker group thereto based on "amino chemistry". Well-known examples of amino chemistry comprise amongst others the reaction of amino groups with so-called activated groups, like NHS-esters, other activated esters, acid chlorides and azides.

Carboxyl groups on biomolecules (the terminal $COO^-$-group, the carboxy functions of glutamic acid or aspartic acid) are used for chemical coupling based on "carboxy chemistry". Well-known examples of carboxy chemistry comprise amongst others the activation of these carboxy groups to carry the above mentioned activated groups. Coupling to e.g., amino groups on the marker is then easily performed.

Alternatively sulfhydryl groups on biomolecules (e.g. free-SH-groups of cysteine or —SH groups obtained by reducing di-sulfhydryl bridges) are used for chemical coupling based on "sulfhydryl chemistry". Well-known examples of sulfhydryl chemistry comprise amongst others the reaction of —SH groups with maleimido groups, or alkylation with α-halogen carboxylic group or by thioethers.

The hydroxyl group of tyrosine residues or the imidazole group of histidine also may be used to covalent link compounds according to the present invention to a biomolecule by aid, e.g., of diazonium groups.

The coupling moiety may be either part of the chemiluminescent heterocycle of Formula I or of the leaving group. It is generally accepted that large biomolecules may interfere with the luminescent light emitted by the chemiluminescent group if both the chemiluminescent group and biomolecule are in close proximity. It is therefore preferred that the coupling group is part of the leaving group and to preferably use such compound for coupling to a biomolecule. In the case such a conjugate is used in a chemiluminescence assay upon release of the chemiluminescent heterocycle from the biomolecule to which the leaving group remains attached, both molecules the luminophore and the biomolecule no longer are in close proximity. This is advantageous in an assay for detection of an analyte in a sample.

The term "biomolecule" comprises molecules and substances of interest in a therapeutic or a diagnostic field. Biomolecule in the sense of the present invention is any naturally occurring or synthetically produced molecule composed of amino acids, nucleotides, nucleosides, lipids, hormones and/or sugars. As the skilled artisan will appreciate non-naturally occurring derivatives e.g., of amino acids, or nucleotides, like artificial amino acids or artificial nucleotides or nucleic acid analogs may also be comprised in a biomolecule without departing from the spirit of this invention.

In a preferred embodiment the biomolecule is selected from the group consisting of polypeptides, nucleic acids, and low molecular weight drugs. Wherein low molecular weight is a molecular weight below 5000 Da.

Especially preferred are biomolecules which function as a specific binding partner for a biological, biochemical or chemical species.

A conjugate between a biomolecule and a chemiluminescent compound according to the present invention, represents a further preferred embodiment. It will be readily appreciated by the skilled artisan that conjugates between a biomolecule and the chemical compounds described in the present invention are of great advantage, e.g., in a specific binding assay for detection of an analyte in a sample.

It is especially preferred to use a compound according to the present invention or a biomolecule-conjugate comprising such compound in an assay employing chemiluminescence detection. Preferably such chemiluminescence based assay is a specific binding assay, e.g. an immunoassay.

Specific binding assays in general are based on the specific interaction of two members of a bioaffine binding pair. Examples of preferred specific binding partners in such binding pairs are hapten or antigen and an antibody reactive thereto, biotin or biotin-analogs such as aminobiotin, iminobiotin, or desthiobiotin which binds to biotin or streptavidin, sugar and lectin nucleic acid or nucleic acid analogs and complementary nucleic acid, receptor and ligand for example steroid hormone receptor and steroid hormone, and enzymes and their substrates.

The specific interaction between nucleic acids (or nucleic acid analogs) and nucleic acids complementary thereto in assays based on detection of hybridization between nucleic acid stands and the specific interaction of antibodies with their respective antigen on which the broad range of immunoassays is based, are most relevant in diagnostic routine.

The theory and practice of nucleic acids hybridization assays is summarized in relevant text books, like Kessler, C., "Non-radioactive labeling and detection of biomolecules", Springer Verlag, Berlin Heidelberg (1992). The skilled artisan will find all relevant details therein.

Immunoassays nowadays are broadly used and general knowledge to the skilled artisan. Relevant methods and procedures are summarized in related text books, like Aslam, M., and Dent, A., Bioconjugation (1998) 216-363, London, and Tijssen, "Practice and theory of enzyme immunoassays" (1990), Amsterdam, Elsevier. A comprehensive review can also be found in an article authored by Mayer, A., and Neuenhofer, S., Angewandte Chem. Intern. Ed. Engl. (1994) 1063-1068, Weinheim, VCH Verlagsgesellschaft mbH.

In a further preferred embodiment the present invention relates to a method of performing a chemiluminescence assay based on the use of a compound according to the present invention. Such chemiluminescence based assay method is characterized in that in the presence of trigger solution luminescent light is emitted and can be measured.

Figure 2:
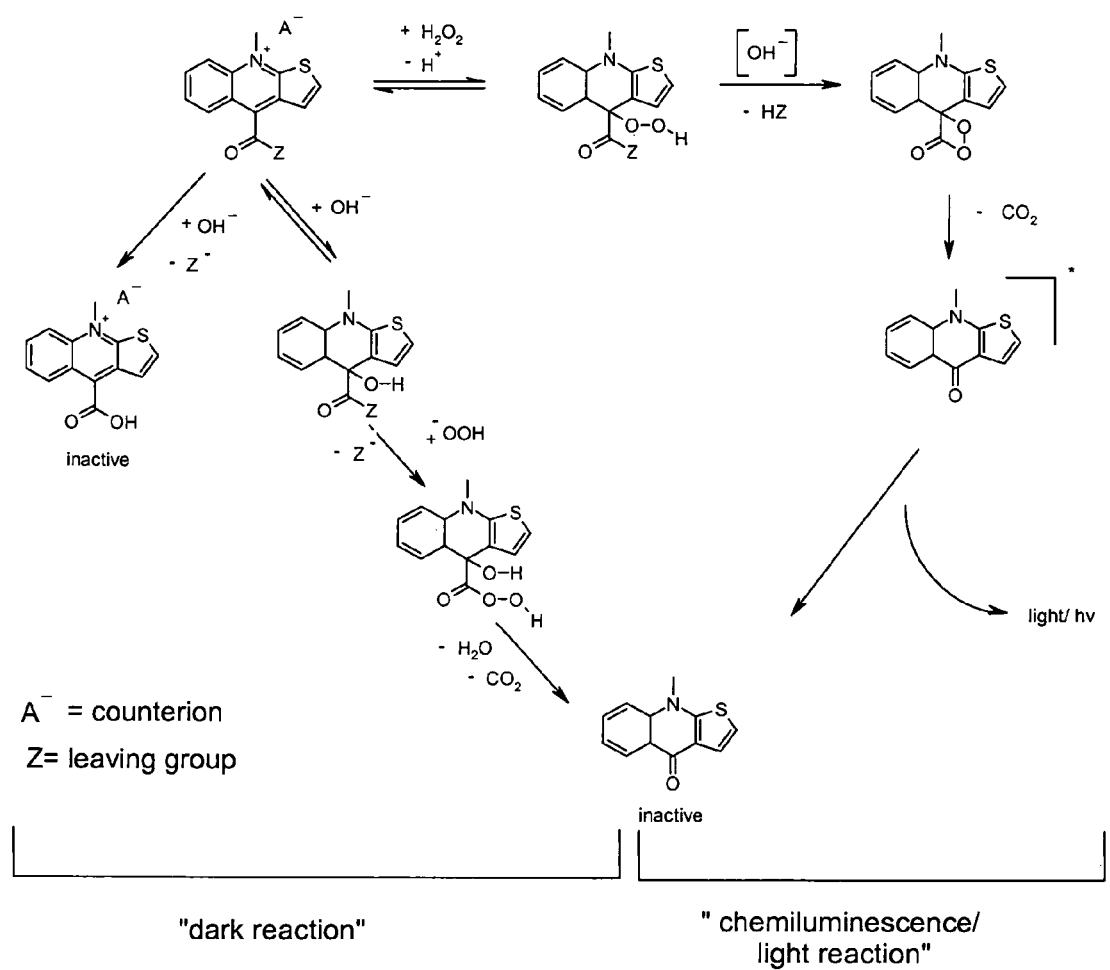
FIG. 2 Mechanism of chemiluminescence for a compound according to Formula I
This schematic represents the likely mechanisms on which chemiluminescence of a compound according to Formula I can be based.

Upon the action of a trigger solution, e.g., peroxide or a reactive oxygen species like the oxygen radical anion the chemiluminescent compound of the present invention most likely according to the mechanism illustrated in FIG. 2 forms a dioxetane intermediate which is decarboxylated to generate an electronically excited emitter. The transition to the ground state of this emitter ensues by emission of a photon (=chemiluminescence). The energy (light) which is thereby emitted is measured according to standard procedures and with routine equipment.

As indicated, $H_2O_2$ or a reactive oxygen species like the oxygen radical anion has to be present to form the intermediate dioxetanone. $H_2O_2$ can be added directly or generated indirectly e.g. by enzymatic reaction (glucose oxidase/glucose). Reactive oxygen species are generated during the chemiluminescent reaction from oxygen or $H_2O_2$. Alternatively, a reactive oxygen species can be generated intentionally e.g. by the oxygen initiated C—C coupling (indoxyl-phosphate, U.S. Pat. No. 5,589,328).

Of course the oxidation conditions, i.e., the trigger solution must be chosen such that no destruction of the light emitting molecule occurs and a maximum of light emission is achieved. Trigger solutions may be set up as a single mixture of trigger reagents or triggering may be based on two separate trigger solutions which if combined trigger chemiluminescence. Trigger solutions in the later case for example are 0.5% H2O2, 0.1 M HNO3 for trigger 1 and 0.25 M NaOH and 0.125% Cetyl trimethyl ammonium chloride (CTAC) for trigger 2.

The generation of the chemiluminescence signal may be accelerated or increased by the use of mediators or enhancers.

Mediators are redox-active compounds which facilitate the oxidation of a compound by accelerating electron transfer processes. The mediator is oxidized by the oxidant and oxidizes then the compounds according to the invention, whereby the mediator is reduced again. Typical mediators are hexocyanoferrate (II) and metal complexes like ferrocene. Other enhancers which are used in chemiluminescence reactions include chemicals like iodo-phenol or phenyl boronic acid.

The oxidation preferably is performed in the presence of an appropriate detergent, which creates a hydrophobic microenvironment around the light emitting heterocyclic ketone. This results in an increase of the chemiluminescence quantum yield since quenching due to interaction with water molecules is reduced. Additionally an appropriate fluorophore, like fluorescein can be attached covalent to the detergent or alternatively a fluorophore can be added to the reaction mixture in order to facilitate an energy transfer from the excited heterocyclic ketone to this fluorophore.

The present invention also relates to a method for synthesizing a compound of Formula I. Preferably such synthesis comprises the steps of activating the carboxyl moiety at position 4 of the central heterocycle according to general Formula VI, e.g., by activation of this moiety e.g. by halogenation, or in situ by dicyclohexylcarbodiimide (DCC) or similar reagents.

Formula VI:

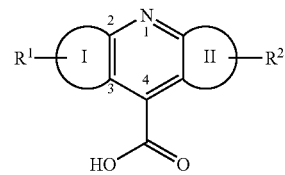

wherein the fused rings I and II as well as residues $R^1$ and $R^2$ are as defined above for Formula I.

Then the leaving group Z is introduced in a dry organic solvent eventually supported by adding a non-nucleophilic base, e.g. pyridine, dimethylaminopyridine (DMAP) and the like. Finally the nitrogen of the heterocyclic ring system at position 1 is alkylated by e.g., methyltriflate, propanesultone or other alkylating reagents.

The following examples, references, and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Synthesis of Furo-quinoline Carboxamide 12

Figure 3:
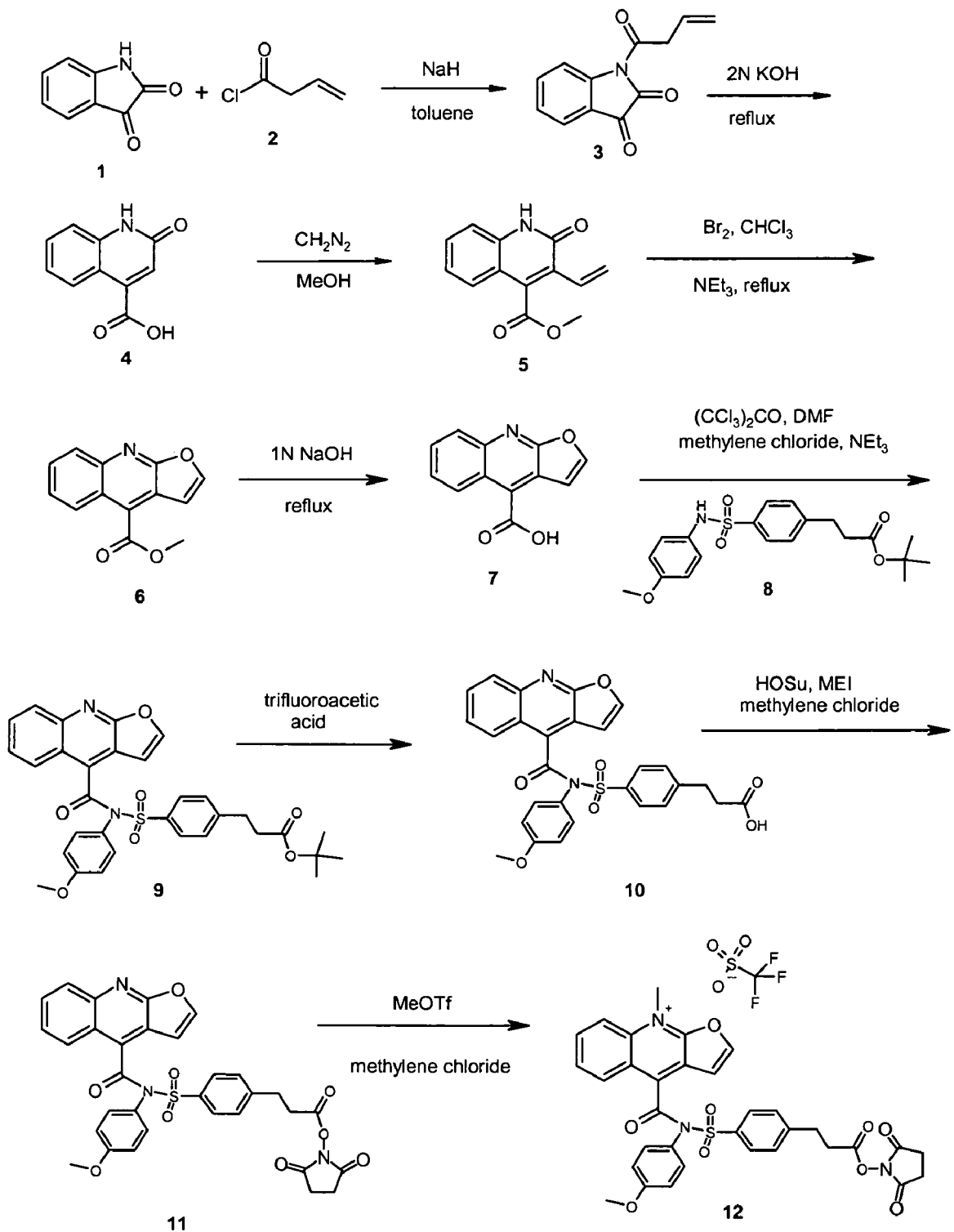
FIG. 3 Synthesis of furo-quinoline carboxamide
This schematic represents the synthesis pathway for Furo-quinoline carboxamide 12 as detailed in Example 1.

The overall synthesis pathway is depicted schematically in FIG. 3.

a) Synthesis of 2-oxo-3-vinyl-1,2-dihydroquinoline-4-carboxylic acid 4

7.9 g (53 mmol) Isatin 1 and 2.36 g sodium hydride (59 mmol, 60% dispersion in mineral oil) were suspended in 500 mL toluene and stirred first for 20 minutes at room temperature and then for half an hour at 110° C. After cooling to ambient temperature a solution of 7.0 g (53 mmol) vinyl acetic acid chloride 2 was added and the mixture was heated again for approx. half an hour at 110° C. Then the reaction mixture was filtered and the resulting filtrate containing N-(3-butenoyl)-isatin 3 was dropped slowly to a boiling solution of 40 mL 2N KOH. After complete addition the mixture was refluxed for another 10 minutes until the reaction was finished. The aqueous layer was separated an acidified with 4N HCl whereupon a brownish solid precipitated, which was filtered off. The brown residue was diluted in 120 mL of a saturated sodium bicarbonate solution, filtered and acidified again with 4N HCl to give a beige precipitate. Filtration and drying under vacuum afforded 4.56 g of 4 as a beige solid.

1H-NMR (d6-Aceton, 300 MHz): δ(ppm)=5.56 (dd, 1H; J=11.3 Hz, J=2.9 Hz); 6.62 (dd, 1H; J=17.3 Hz, J=2.9 Hz); 6.76 (dd, 1H; J=11.3 Hz, J=17.3 Hz); 7.27 (m, 1H); 7.47 (m, 1H); 7.56 (m, 2H); Rf (n-butanol/acetic acid/water 10:3:5)=0.60 b) Synthesis of methyl-2-oxo-3-vinyl-1,2-dihydroquinoline-4-carboxylate 5

To a solution of 4.4 g (20 mmol) 2-Oxo-3-vinyl-1,2-dihydroquinoline-4-carboxylic acid 4 in 200 mL methanol was added etheral diazomethane at ambient temperature until the vigorous evolution of nitrogen subsided and the starting material was used up. Then 10 mL acetic acid were added, the mixture was diluted with 200 mL diethylether and washed with a solution of sodium bicarbonate (5%) and brine. The organic layer was separated, dried over sodium sulfate and filtered. After evaporation the crude product was purified by chromatography on silica gel eluting with toluene/ethyl acetate/methanol 4:1:1, to give 2.6 g of 5 as a pale yellow solid.

1H-NMR (d6-Aceton, 300 MHz): δ(ppm)=4.03 (s, 3H); 5.55 (dd, 1H; J=11.2 Hz, J=2.8 Hz); 6.51 (dd, 1H; J=17.3 Hz, J=2.8 Hz); 6.66 (dd, 1H; J=11.2 Hz, J=17.3 Hz); 7.22 (m, 1H); 7.45 (m, 2H); 7.57 (m, 1H); Rf (toluene/ethyl acetate/methanol 4:1:1)=0.56 c) Synthesis of Methyl-furo[2,3-b]quinoline-4-carboxylate 6

To a solution of 2.6 g (11.2 mmol) Methyl-2-oxo-3-vinyl-1,2-dihydroquinoline-4-carboxylate 5 in 200 mL chloroform was added slowly over a dropping funnel a solution of 2.16 g (13.5 mmol) bromine in 15 mL chloroform and subsequently 6.8 mL of triethylamine. The reaction mixture was heated at reflux for 4.5 hour. After evaporation of the solvent the residue was purified by column chromatography on silica gel, eluting with toluene/ethyl acetate/methanol 4:1:1, to give 1.1 g of the desired product 6.

1H-NMR (d6-Aceton, 300 MHz): δ(ppm)=4.15 (s, 3H); 7.37 (d, 1H; J=2.7 Hz); 7.70 (m, 1H); 7.83 (m, 1H); 8.12 (m, 1H); 8.27 (d, 1H; J=2.7 Hz); 8.87 (m, 1H); Rf (toluene/ethyl acetate/methanol 4:1:1)=0.75 d) Synthesis of Furo[2,3-b]quinoline-4-carboxylic acid 7

A mixture of 1.0 g (4.3 mmol) Methyl-furo[2,3-b]quinoline-4-carboxylate 6, 12 ml methanol and 60 mL 1N NaOH was heated at reflux for 75 minutes. After cooling the solution was acidified with 4N HCl to pH ~1-2, whereupon a solid precipitated. Then the reaction mixture was extracted with 200 mL diethylether. The organic layer was separated and extracted now with 150 mL of a sodium bicarbonate solution (5%), wich was acidified another time with 4N HCl to give the product 7 as a crystalline solid. The precipitate was filtered and dried under vacuum to give 760 mg of 7.

1H-NMR (d6-Aceton, 300 MHz): δ(ppm)=7.46 (d, 1H; J=2.6 Hz); 7.69 (m, 1H); 7.83 (m, 1H); 8.14 (m, 1H); 8.26 (d, 1H; J=2.6 Hz); 8.96 (m, 1H); Rf (chloroform/methanol/acetic acid 7:3:0.1)=0.42 e) Synthesis of tert-butyl-3-[4-(4-methoxy-phenylsulfamoyl)-phenyl]-propionate 8

A mixture of 6.0 g (24.1 mmol) 3-(4-Chlorsulfonylphenyl)-propionic acid, 4 mL tert-butanol, 0.84 mL concentrated sulfuric acid and 4 mL isobutene was placed in an autoclave and stirred for 24 hours at room temperature. Then the reaction mixture was diluted with 250 mL of a saturated sodium bicarbonate solution and extracted three times with 100 mL methylene chloride. The combined organic phases were dried over sodium sulfate, filtered and concentrated under vacuum to give a brownish oil. The crude intermediate was diluted with 140 mL hot hexane, filtered and evaporated to yield a beige solid which was directly dissolved in 50 mL methylene chloride. Then 2.02 g p-anisidine and 250 mg 4-dimethylaminopyridine (DMAP) were added and stirred for 2.5 hours at ambient temperature. After evaporation of the solvent the brown residue was purified by column chromatography on silica gel (eluent: toluene/methanol 4:1). The fractions containing the product were combined, evaporated and dried under vacuum to yield 2.3 g of 8 as a white solid.

Rf (toluene/methanol 4:1)=0.37 f) Synthesis of N-(4-methoxy-phenyl)-N-(tert-butyl-oxycarbonylpropyl-sulfonyl)-furo[2,3-b]quinoline-4-carboxamide 9

156 mg (0.525 mmol) Bis(trichloromethyl) carbonate (triphosgene) were dissolved in 2.0 mL of dry methylene chloride under argon and 110 µl DMF (1.43 mmol) were added at 0° C. The reaction mixture was stirred for 75 minutes on an ice-bath and warmed to room temperature. Then a suspension of 323 mg (1.5 mmol) furo[2,3-b]quinoline-4-carboxylic acid 7 in 5 mL methylene chloride, 520 mg (1.5 mmol) tert-butyl-3-[4-(4-methoxy-phenylsulfamoyl)-phenyl]-propionate 8 in 5 mL methylene chloride and 455 µl triethylamine (3.27 mmol) were added. The mixture was stirred subsequently for 1.5 hours at ambient temperature, dilute with 20 mL methylene chloride and washed with 10 mL brine and 20 mL water. The organic phase was separated, dried over sodium sulfate and filtered. The crude product was purified by column chromatography on silica gel (eluent: methylene chloride/diisopropylether 7:3). The fractions containing the product were combined, evaporated and dried under vacuum to yield 200 mg of 9.

1H-NMR (d6-Aceton, 300 MHz): δ(ppm)=1.41 (s, 9H); 2.70 (m, 2H); 3.11 (m, 4H); 3.59 (s, 3H); 6.58 (m, 2H); 7.05 (d, 1H; J=2.7 Hz); 7.11 (m, 2H); 7.65 (m, 3H); 7.76 (m, 1H); 7.81 (m, 1H); 7.96 (m, 1H); 8.10 (m, 2H) 8.15 (d, 1H; J=2.7 Hz); Rf (methylene chloride/diisopropylether 7:3)=0.48 g) Synthesis of N-(4-Methoxy-phenyl)-N-(carboxypropyl-sulfonyl)-furo[2,3-b]quinoline-4-carboxamide 10

200 mg (0.34 mmol) N-(4-Methoxy-phenyl)-N-(tert-butyl-oxycarbonylpropyl-sulfonyl)-furo[2,3-b]quinoline-4-carboxamide 9 were dissolved in 3.0 mL trifluoroacetic acid and stirred for 15 minutes at room temperature. The solvent was removed under reduced pressure to give an yellow oil. The residue was purified by silica gel chromatography (eluent: methylene chloride/diethylether 6:4+0.1% acetic acid). Evaporation of the appropriate fractions gave 140 mg of the desired product 10.

Rf (methylene chloride/diethylether 6:4+0.1% acetic acid)=0.34 h) Synthesis of N-(4-methoxy-phenyl)-N-(succinimidyl-oxycarbonyl-propyl-sulfonyl)-furo[2,3-b]quinoline-4-carboxamide 11

A mixture of 140 mg (0.26 mmol) N-(4-Methoxy-phenyl)-N-(carboxypropyl-sulfonyl)-furo[2,3-b]quinoline-4-carboxamide 10, 54 µl (0.37 mmol) 2-Morpholino-ethyl-isocyanide (MEI) and 44 mg (0.37 mmol) N-Hydroxysuccinimide (HOSu) was stirred overnight at room temperature. The solvent was removed under vacuum and the oily residue was purified by silica gel column chromatography (eluent: methylene chloride/acetone 9:1+0.1% acetic acid). The appropriate fractions were combined and evaporated to yield 94 mg of 11.

Rf (methylene chloride/acetone 9:1+0.1% acetic acid)=0.40 i) Synthesis of N1-methyl-N-(4-Methoxy-phenyl)-N-(succinimidyl-oxycarbonyl-propyl-sulfonyl)-furo[2,3-b]quinolinium-4-carboxamide 12

To a solution of 94 mg (0.15 mmol) N-(4-Methoxy-phenyl)-N-(succinimidyl-oxycarbonyl-propyl-sulfonyl)-furo[2,3-b]quinoline-4-carboxamide 11 in 4 mL methylene chloride were added 130 µL methyl triflate and the reaction mixture was stirred for 1.75 hours at ambient temperature. Removal of the solvent gave a yellow, oily residue which was purified by column chromatography on silica gel eluting with methylene chloride/acetonitrile 1:1+0.1% acetic acid. Evaporation and drying of the appropriate fractions yielded 69 mg of the product 12.

MS: ESI: M+=642.08; 1H-NMR (d6-Aceton, 300 MHz): δ(ppm)=2.91 (m, 4H); 3.16 (m, 2H); 3.28 (m, 4H); 3.84 (s, 3H); 4.76 (s, 3H); 6.75 (m, 2H); 7.35 (m, 2H); 7.62 (d, 1H; J=2.5 Hz); 7.75 (m, 2H); 8.00 (m, 2H); 8.10 (m, 1H); 8.24 (m, 1H); 8.38 (m, 1H) 8.64 (d, 1H; J=2.5 Hz); Rf (methylene chloride/acetonitrile 1:1+0.1% acetic acid)=0.21

Example 2

Synthesis of Thieno-quinoline Carboxamide 19

Figure 4:
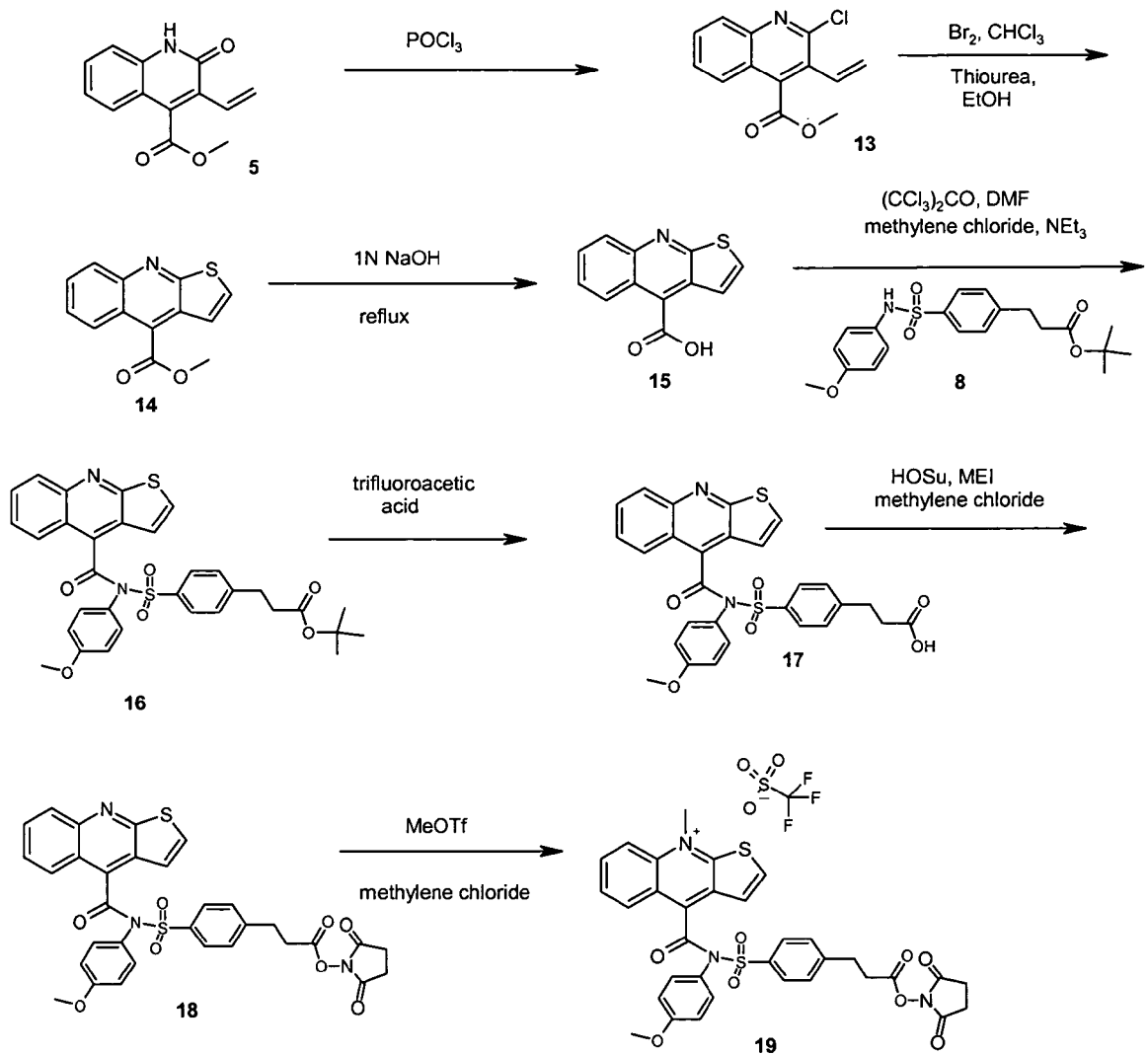
FIG. 4 Synthesis of thieno-quinoline carboxamide
This schematic represents the synthesis pathway for Thieno-quinoline carboxamide 19 as detailed in Example 2.

A schematic representation of this synthesis can be found in FIG. 4.

a) Synthesis of methyl-2-chloro-3-vinyl-quinoline-4-carboxylate 13

2.3 g (10 mmol) methyl-2-oxo-3-vinyl-1,2-dihydroquinoline-4-carboxylate 5 were dissolved in 5.5 mL phosphorus oxychloride and heated for 45 min at 105° C. After cooling, the mixture was poured into ice-water (~80 ml) and the pH-value was adjusted with an ammonium hydroxide solution (25%) to 7-8. After extraction with 100 mL chloroform, the organic phase was washed with water and brine, separated and dried over sodium sulfate. Filtration and evaporation gave a brown oily residue which was purified by silica gel column chromatography (eluent: methylene chloride/acetone 9:1). The appropriate fractions were combined and evaporated under reduced pressure. The brown oil was recrystallized from n-hexane to yield 1.90 g of 12 as colourless needles Rf (methylene chloride/acetone 9:1)=0.84 b) Synthesis of methyl-thieno[2,3-b]quinoline-4-carboxylate 14

To a mixture of 1.8 g (7.2 mmol) Methyl-2-oxo-3-vinyl-1,2-dihydroquinoline-4-carboxylate 5 in 40 mL chloroform was added slowly over a dropping funnel a solution of 1.15 g (7.2 mmol) bromine in 40 mL chloroform and the reaction mixture was stirred for 1 hour at ambient temperature. After evaporation of the solvent the residue was mixed with 40 mL ethanol and 1.7 g (18 mmol) thiourea and refluxed for 2.5 h. After cooling the mixture was poured on ice, the pH-value was adjusted with ammonium hydroxide at pH=7-8 and the solution was extracted with 100 mL chloroform. The organic layer was separated, dried over sodium sulfate and filtered. Then the solvent was removed under reduced pressure and the crude product was purified by column chromatography on silica gel, eluting with methylene chloride/acetone 9:1, to give 1.0 of the desired product 14.

MS: ESI: M+=242.82; Rf (methylene chloride/acetone 9:1)=0.80 c) Synthesis of thieno[2,3-b]quinoline-4-carboxylic acid 15

1.0 g (4.1 mmol) methyl-thieno[2,3-b]quinoline-4-carboxylate 14, 12 ml ethanol and 60 mL 1N NaOH were mixed and heated at reflux for 75 minutes. After cooling the green solution was acidified with 4N HCl to pH ~1-2, whereupon a solid precipitated. Then the reaction mixture was extracted with 200 mL diethylether. The organic layer was separated and extracted now with 150 mL of a sodium bicarbonate solution (5%), which was acidified another time with 4N HCl to give the product 15 as a crystalline solid. The precipitate was filtered off and dried under vacuum to give 760 mg of 15.

Rf (chloroform/methanol/acetic acid 7:3:0.1)=0.21 d) Synthesis of N-(4-methoxy-phenyl)-N-(tert-butyl-oxycarbonylpropyl-sulfonyl)-thieno[2,3-b]quinoline-4-carboxamide 16

156 mg (0.525 mmol) bis(trichloromethyl) carbonate (triphosgene) were dissolved in 2.0 mL of dry methylene chloride under argon and 110 µl DMF (1.43 mmol) were added at 0° C. The reaction mixture was stirred for 1.5 hours on an ice-bath and warmed to room temperature. Then a suspension of 300 mg (1.2 mmol) Thieno[2,3-b]quinoline-4-carboxylic acid 15 in 5 mL methylene chloride, 470 mg (1.2 mmol) tert-butyl-3-[4-(4-methoxy-phenylsulfamoyl)-phenyl)]-propionate 8 in 5 mL methylene chloride and 455 µl triethylamine (3.27 mmol) were added. The mixture was stirred subsequently for 1.5 hours at ambient temperature, dilute with 5 mL methylene chloride and washed with 10 mL water. The organic phase was separated, dried over sodium sulfate and filtered. After evaporation of the solvent the crude product was purified by silica gel chromatography (eluent: methylene chloride/diisopropylether 7:3). The fractions containing the product were combined, evaporated and dried under vacuum to give 80 mg of 16.

Rf (methylene chloride/diisopropylether 7:3)=0.48 e) Synthesis of N-(4-Methoxy-phenyl)-N-(carboxypropyl-sulfonyl)-thieno[2,3-b]quinoline-4-carboxamide 17

80 mg (0.13 mmol) N-(4-Methoxy-phenyl)-N-(tert-butyl-oxycarbonylpropyl-sulfonyl)-thieno-[2,3-b]quinoline-4-carboxamide 16 were dissolved in 1.2 mL trifluoroacetic acid and stirred for 30 minutes at room temperature. 50 mg of silica gel and 10 mL of methylene chloride were added and the solvent was removed under reduced pressure. The residue was purified by chromatography on silica gel (eluent: methylene chloride/diethylether 6:4+0.1% trifluoroacetic acid). Evaporation of the appropriate fractions gave 66 mg of the desired product 17.

Rf (methylene chloride/diethylether 6:4+0.1% acetic acid)=0.51 f) Synthesis of N-(4-Methoxy-phenyl)-N-(succinimidyl-oxycarbonyl-propyl-sulfonyl)-thieno[2,3-b]quinoline-4-carboxamide 18

A mixture of 66 mg (0.12 mmol) N-(4-Methoxy-phenyl)-N-(carboxypropyl-sulfonyl)-thieno[2,3-b]quinoline-4-carboxamide 17, 25 µl (0.17 mmol) 2-Morpholino-ethyl-isocyanide (MEI) and 21 mg (0.17 mmol) N-Hydroxysuccinimide (HOSu) was stirred overnight at room temperature. The solvent was removed under vacuum and the oily residue was purified by silica gel column chromatography (eluent: methylene chloride/acetone 9:1+0.1% acetic acid). The appropriate fractions were combined and evaporated to yield 75 mg of 18.

Rf (methylene chloride/acetone 9:1+0.1% acetic acid)=0.42 g) Synthesis of N1-methyl-N-(4-Methoxy-phenyl)-N-(succinimidyl-oxycarbonyl-propyl-sulfonyl)-thieno[2,3-b]quinolinium-4-carboxamide 19

To a solution of 75 mg (0.12 mmol) N-(4-Methoxy-phenyl)-N-(succinimidyl-oxycarbonyl-propyl-sulfonyl)-thieno[2,3-b]quinoline-4-carboxamide 18 in 3 mL methylene chloride were added 100 μL methyl triflate and the reaction mixture was stirred for 2 hours at ambient temperature. After removal of the solvent the crude product was purified by column chromatography on silica gel eluting with methylene chloride/acetonitrile 6:4+0.2% acetic acid. Evaporation and drying of the appropriate fractions gave 65 mg of the product 19.

MS: ESI: M+=657.88; 1H-NMR (d6-Aceton, 300 MHz): δ(ppm)=2.53 (m, 2H); 2.82 (m, 4H); 2.91 (m, 4H);); 3.19 (m, 2H); 3.27 (m, 4H); 3.78 (bs, 3H); 4.93 (bs, 3H); 6.73 (m, 2H); 7.33 (m, 2H); 7.73 (m, 4H); 8.14 (m, 1H); 8.39 (m, 4H); 8.76 (m, 1H). Rf (methylene chloride/acetonitrile 6:4+0.2% acetic acid)=0.21

Example 3

Evaluation of Thieno-quinoline Carboxamide 19: Kinetics, Sensitivity

Measurements were performed on a Berthold Lumat LB 953. Two triggers have been used to produce chemiluminescence, both promoting CL-reaction.

Trigger 1: 300 μL; 0.5% H2O2, 0.1 M HNO3
Trigger 2: 300 μL; 0.25 M NaOH, 0.125% Cetyl trimethyl ammonium chloride (CTAC)

Thieno-quinoline carboxamide 19 was diluted to 1×10-9 Mol/L in PBS-buffer containing 0.1% Thesit. 100 μL sample was dispensed in a 5 mL Sarsted tube and set into the instrument. Trigger 1 was added in position −1, trigger 2 in the measuring position. Measurement was performed for 10 sec.

Figure 5:
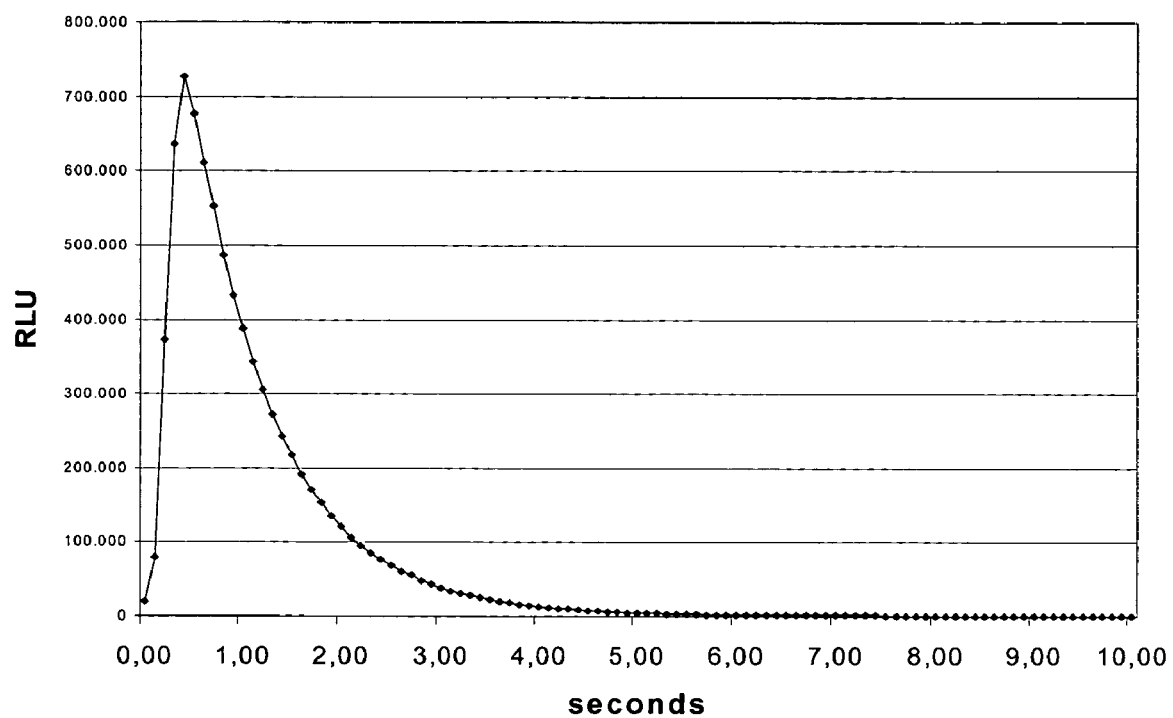
FIG. 5 Chemiluminescence of thieno-quinoline carboxamide 19
Shown is the chemiluminescence (in relative light units (RLU)) of Thieno-quinoline carboxamide 19. The active ester had been used at a concentration of 1×10-9 mol/l.

The kinetics of light emission for this compound under the above conditions is shown in FIG. 5:

Sensitivity:

A serial dilution of Thieno-quinoline carboxamide 19 in PBS-buffer containing 0.1% Thesit was performed. Each sample was measured as described above, except for the measuring time which was only 2 sec. The smallest signal still significantly different from the blank was considered as the lower detection limit.

This way the lower detection limit has been found to be $1\times10^{-12}$ Mol/L.

Example 4

Preparation of an Anti-TSH Conjugate Based on Thieno-quinoline Carboxamide 19 and a Monoclonal Antibody Against TSH A solution of a monoclonal anti-TSH antibody (10 mg; 0.066 μmol) in 1 mL of 0.05 M phosphate buffer, pH 7.8 was treated with a solution of thieno-quinoline carboxamide 19 (108 μg; 0.134 μmol) in 50 μL dimethylsulfoxide at room temperature for 1.5 hours. The conjugation was stopped by adding a 10.5 μl of a solution of lysine (1M) in water. Then the pH-value was adjusted with 1M K₂HPO₄ to pH 7.8 the conjugate was purified by passing the reaction mixture through a HiLoad 16/60 Superdex® 200 pg column packed and eluted with 0.05 M phosphate buffer, pH 6.8. The elution was monitored at 280 nm with an Amersham Pharmacia ÄKTA Explorer UV-900 Detector. The appropriate fractions were collected and dried by lyophilization to yield 5.97 mg of the desired conjugate.

This conjugate has been used in a preliminary assay set-up for the detection of TSH. It has been found that this conjugate is appropriate for detection of TSH in clinical samples.

What is claimed is:

1. A compound according to the formula:

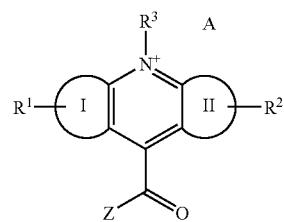

wherein one of the fused rings I and II is phenyl and the other is an aromatic five ring heterocycle having one heteroatom, $R^1$ and $R^2$ are independently selected from the group consisting of hydrogen, R, halogen, —NR₂, —OR, —OH, —S(O)₂OH, —CN, —SCN, —SSR, —SR, —C(O)R, —C(O)H, —C(O)OR, —C(O)OH, —NHC(O)R, —C(O)NHR, —C(O)NH₂, —S(O)₂NHR, and —S(O)₂NH₂;

R is selected from the group consisting of alkyl, alkenyl, alkynyl, and aralkyl, wherein said alkyl, alkenyl or alkynyl can contain up to 20 heteroatoms;

$R^3$ is selected from the group consisting of alkyl, alkenyl, alkynyl, and alkyl, alkenyl, alkynyl, aralkyl groups that further comprise a coupling moiety, wherein said alkyl, alkenyl, or alkynyl can contain up to 20 heteroatoms;

A comprises a counter-ion to balance a net charge of the compound; and

Z comprises a leaving group selected from the group consisting of —O—V, —S—V, —N(V)—SO₂—V', —O—N(V)—SO₂—V', —S—N(V)—V', —O—N(V)—C(O)—V', —O—N=C(V)—V', and —O—N=C(V)—Cl, wherein V and V' are independently selected from the group consisting of alkyl, substituted alkyl, and an aryl moiety corresponding to the formula:

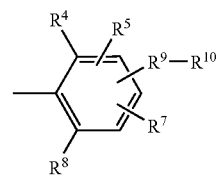

with the proviso that at least one of V or V' must be the aryl moiety and wherein said substituted alkyl is substituted with one or more compounds selected from the group consisting of —S(O)₂OH, fluorine, and chlorine.

2. The compound of claim 1 wherein $R^3$ is selected from the group consisting of methyl, ethyl, sulfopropyl, and sulfobutyl.

3. The compound of claim 1 wherein:

the aromatic five ring heterocycle is selected from the group consisting of pyrrole, thiophene, and furan;

$R^3$ is selected from the group consisting of methyl, ethyl, sulfopropyl, and sulfobutyl; and R$^1$ and R$^2$ are independently selected from the group consisting of hydrogen, fluorine, chlorine, —OH, —C(O)CH$_3$, —S(O)$_2$OH, and —S(O)$_2$NH$_2$.

4. The compound according to claim 1 wherein:

R$_3$ is selected from the group consisting of alkyl, alkenyl, alkynyl, and aralkyl, wherein said alkyl, alkenyl or alkynyl can contain up to 20 heteroatoms; and Z further comprises a coupling moiety.

5. The compound according to claim 4 wherein said coupling moiety is selected from the group consisting of N-succinimidyl-oxycarbonyl, maleinimido, 4,6-dichloro-[1,3,5]triazin-2-amino-, N-benzotriazolyl-oxycarbonyl, N-phtalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —SO$_2$Cl, —SO$_2$Br, —SO$_2$I, —NH$_2$, —N$_3$, —N=C=O, —N=C=S, —N$_2$$^+$, —Cl, —Br, and —I.

6. The compound according to claim 5 wherein R$^1$ and R$^2$ are each hydrogen, and R$^3$ is selected from the group consisting of methyl, ethyl, sulfopropyl, and sulfobutyl.

7. The compound according to claim 1 represented by the structure:

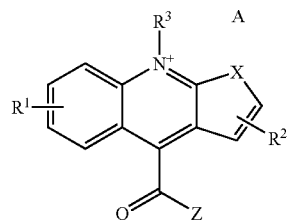

wherein R$^1$ and R$^2$ are independently selected from the group consisting of hydrogen, fluorine, chlorine, —OH, —C(O)CH$_3$, —S(O)$_2$OH, and —S(O)$_2$NH$_2$;

R$^3$ is selected from the group consisting of alkyl, sulfoalkyl, and alkylamidoalkyl;

A comprises a counter—ion to balance a net charge of the compound;

X is selected from the group consisting of —N—, —O—, and —S—; and

Z is selected from the group consisting of —O—V, —S—V, —N(V)—S$_2$—V', —O—N(V)—S$_2$—V', —S—N(V)—V', —O—N(V)—C(O)—V', —O—N=C(V)—V', and —O—N=C(V)—Cl, wherein V and V' are independently selected from the group consisting of alkyl, substituted alkyl, and an aryl moiety corresponding to the formula:

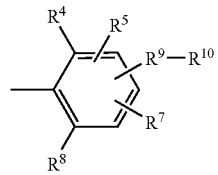

with the proviso that at least one of V or V' must be the aryl moiety and wherein said substituted alkyl is substituted with one or more compounds selected from the group consisting of —S(O)$_2$OH, fluorine, and chlorine;

R$^4$ and R$^8$ are independently selected from the group consisting of hydrogen, halogen, alkyl, alkenyl, alkynyl, alkoxy, alkylsulfanyl, and alkylamido;

R$^5$ and R$^7$ are independently selected from the group consisting of hydrogen, fluorine, chlorine, —OH, —C(O)CH$_3$, —S(O)$_2$OH, —S(O)$_2$NH$_2$, and —S(O)$_2$NH$_2$;

R$^9$ is selected from the group consisting of a bond, an electron-withdrawing group, alkyl, alkenyl, alkynyl, and alkylamido, wherein said alkyl, alkenyl, or alkynyl can contain up to 20 heteroatoms; and R$^{10}$ is selected from the group consisting of hydrogen and a coupling moiety, with the proviso that a coupling moiety is present only once in said compound.

8. The compound according to claim 7 wherein

Z is —NV—SO$_2$—V';

R$^3$ is alkyl;

V comprises a compound of the formula:

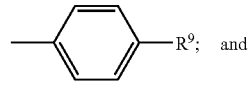

V' comprises a compound of the formula:

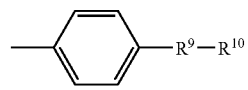

wherein R$^9$ is selected from the group consisting of alkyl, alkenyl, alkynyl, and alkoxy, and R$^{10}$ comprises a coupling moiety.

9. The compound according to claim 8 wherein R$^1$ and R$^2$ are each hydrogen, and R$^3$ is selected from the group consisting of methyl, ethyl, sulfopropyl, and sulfobutyl.

10. The compound according to claim 9 wherein the coupling moiety is selected from the group consisting of N-succinimidyl-oxycarbonyl, N-benzotriazolyl-oxycarbonyl, maleinimido, N-phtalimidyl-oxycarbonyl, p-nitrophenyl-oxycarbonyl, pentafluorophenyl-oxycarbonyl, imidate, p-aminobenzoyl, —C(O)Cl, —C(O)Br, —SO$_2$Cl, —NH$_2$, and —N$_3$.

11. The compound according to claim 10 wherein the coupling moiety is N-succinimidyl-oxycarbonyl or —SO$_2$Cl.

12. A conjugate comprising a compound according to claim 1 and a biomolecule.

13. The conjugate according to claim 12 wherein the biomolecule is a specific binding partner.

14. A method for synthesizing the compound of claim 1 comprising the steps of:

(a) activating the carboxyl group at position 4 of a compound of the formula:

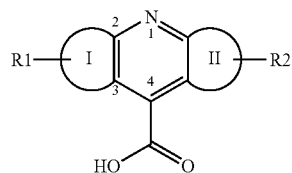

wherein, one of the fused rings I and II is phenyl and the other is an aromatic five ring heterocycle having one heteroatom, R$^1$ and R$^2$ are independently selected from the group consisting of hydrogen, R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR, and —S(O)$_2$NH$_2$; and R is selected from the group consisting of alkyl, alkenyl, alkynyl, and aralkyl, wherein said alkyl, alkenyl, or alkynyl can contain up to 20 heteroatoms;

R is selected from the group consisting of alkyl, alkenyl, alkynyl, and aralkyl, wherein said alkyl, alkenyl, or alkynyl can contain up to 20 heteroatoms;

(b) introducing the leaving group Z at the carboxylic acid after activating the carboxylic acid; and (c) alkylating the N-position 1 of the central heterocycle with a moiety from the group consisting of alkyl, alkenyl, alkynyl, and alkyl, alkenyl, alkynyl, aralkyl groups that further comprise a coupling moiety, wherein said alkyl, alkenyl, or alkynyl can contain up to 20 heteroatoms.

* * * * *